United States Patent [19]

Augstein et al.

[11] 4,064,256

[45] Dec. 20, 1977

[54] BENZOPYRANYLTETRAZOLES AS ANTIASTHMA AGENTS

[75] Inventors: Joachim Augstein, Linford; Hugh Cairns, Loughborough; Dennis Hunter, Loughborough; John King, Loughborough, all of England

[73] Assignee: Fisons Limited, England

[21] Appl. No.: 539,437

[22] Filed: Jan. 3, 1975

Related U.S. Application Data

[62] Division of Ser. No. 175,392, Aug. 26, 1971, Pat. No. 3,933,845.

[30] Foreign Application Priority Data

Aug. 26, 1970 United Kingdom .............. 41009/70
Jan. 13, 1971 United Kingdom ................ 1642/71
July 1, 1971 United Kingdom .............. 30827/71

[51] Int. Cl.² ............................................. A61K 31/41
[52] U.S. Cl. .................................................. 424/269
[58] Field of Search .................... 260/308 R, 247.5 E, 260/293.58; 424/269, 248, 267

[56] References Cited

U.S. PATENT DOCUMENTS 3,427,324 2/1969 Fitzmaurice ...................... 260/340.7
3,706,768 12/1972 Bays .................................. 260/308 D
3,839,339 10/1974 Ellis et al. ........................ 260/308 D

FOREIGN PATENT DOCUMENTS 4,767 1/1967 France ............................... 260/340.7

OTHER PUBLICATIONS

Buchanan et al., J. Med. Chem., vol. 12, pp. 1001–1006 (1969).
Juby et al., I, J. Med. Chem., vol. 11, pp. 111–117 (1968).
Juby et al., II, J. Med. Chem., vol. 12, pp. 396–401 (1969).

Primary Examiner—Raymond V. Rush
Attorney, Agent, or Firm—Wenderoth, Lind & Ponack

[57] ABSTRACT

There are described compounds of formula I,

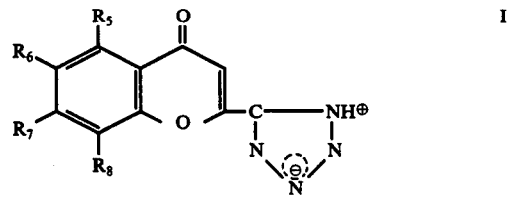

in which $R_5$, $R_6$, $R_7$ and $R_8$, which may be the same or different, are hydrogen, alkyl C2 to 6, alkoxy C2 to 8, hydroxy-alkoxy C3 to 8, and $R_5$ may be hydroxy, provided that one or two of $R_5$, $R_6$, $R_7$ and $R_8$ are other than hydrogen, and pharmaceutically acceptable derivatives thereof. The compounds of formula I are indicated for use in the treatment of asthma, and pharmaceutical compositions containing them and processes for their preparation are also described.

4 Claims, No Drawings

BENZOPYRANYLTETRAZOLES AS ANTIASTHMA AGENTS

This is a division of application Ser. No. 175,392, filed Aug. 26, 1971, now U.S. Pat. No. 3,933,845.

This invention relates to new tetrazole derivatives, compositions containing them and methods for their preparation.

According to our invention we provide compounds of formula I,

[Formula I: benzopyranyltetrazole structure with $R_5$, $R_6$, $R_7$, $R_8$ substituents, $H^\oplus$]

in which $R_5$, $R_6$, $R_7$ and $R_8$, which may be the same or different, are hydrogen, alkyl containing 2 to 6 carbon atoms, alkoxy containing 2 to 8 carbon atoms, hydroxyalkoxy containing 3 to 8 carbon atoms, and $R_5$ may be hydroxy, provided one or two of $R_5$, $R_6$, $R_7$ and $R_8$ are other than hydrogen, and pharmaceutically acceptable derivatives thereof.

According to our invention we also provide a process for the production of a compound of formula I, or a pharmaceutically acceptable derivative thereof, which comprises a. treating a compound of formula II, $$R - Y \quad \text{II}$$

in which R represents a group of formula IX,

[Formula IX: benzopyranyl structure with $R_5$, $R_6$, $R_7$, $R_8$]

in which $R_5$, $R_6$, $R_7$, $R_8$ and the proviso are as defined above, Y represents a group —CN or —CZ=NH, and Z represents a good leaving group, with an azide in a solvent which is inert under the reaction conditions, b. replacing with hydrogen the group X in a compound of formula VII or XIV,

[Formula VII: R—C—N—X tetrazole ring structure]

[Formula XIV: R—C=N tetrazole ring structure with N—X]

in which R is as defined above, and X represents a group which may be replaced by hydrogen, by hydrogenation, dealkylation, deacylation, under mildly basic conditions, under acidic conditions, or by reductive deamination, c. cyclising a compound of formula VIII,

[Formula VIII: structure with $R_5$, $R_6$, $R_7$, $R_8$, CO—CH=C—OH, tetrazole, $H^\oplus$]

or a salt thereof in which $R_5$, $R_6$, $R_7$, $R_8$ and the proviso are as defined above, d. selectively dehydrogenating a compound of formula XV,

[Formula XV: structure with $R_5$, $R_6$, $R_7$, $R_8$, tetrazole, $H^\oplus$]

or a salt thereof in which $R_5$, $R_6$, $R_7$, $R_8$ and the proviso are as defined above, e. producing a compound of formula Ie,

[Formula Ie: structure with $R_5^e$, $R_6^e$, $R_7^e$, $R_8^e$, tetrazole, $H^\oplus$]

in which $R_5^e$, $R_6^e$, $R_7^e$ and $R_8^e$ have the same significances as $R_5$, $R_6$, $R_7$ and $R_8$ above, save at least one of $R_5^e$, $R_6^e$, $R_7^e$ and $R_8^e$ represents an alkyl or alkoxy group, by selective hydrogenation of a corresponding compound of formula XVI,

[Formula XVI: structure with $R_5^b$, $R_6^b$, $R_7^b$, $R_8^b$, tetrazole, $H^\oplus$]

in which $R_5^b$, $R_6^b$, $R_7^b$ and $R_8^b$ have the same significances as $R_5$, $R_6$, $R_7$, and $R_8$ above, save that at least one of $R_5^b$, $R_6^b$, $R_7^b$ and $R_8^b$ represents an alkenyl or an alkenyloxy group, f. producing a compound of formula If,

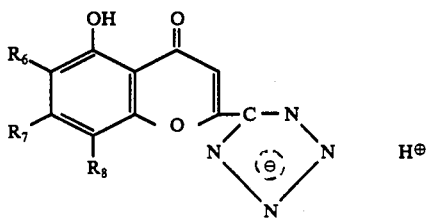

If in which R₅, R₆, R₇, R₈ and the proviso are as defined above, by replacing an R⁹ group with a hydrogen atom in a corresponding compound of formula XVII,

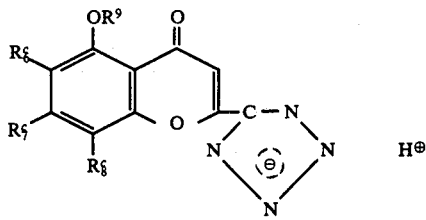

XVII in which R₅, R₆, R₇, R₈ and the proviso are as defined above, and R⁹ represents alkyl, aralkyl or acyl; or g. transforming a compound of formula XVIII,

   XVIII in which R is as defined above into a compound of formula I, and where desired or necessary converting the compound of formula I produced by any one of processes (a) to (g) into a pharmaceutically acceptable derivative thereof.

Suitable solvents which are inert under the reaction conditions of process (a) include those in which both the reagents are soluble, e.g. N,N-dimethylformamide. Other solvents which may be mentioned include dimethylsulphoxide, tetrahydrofuran, diethyl glycol and ethyl methyl glycol. The reaction is preferably carried out at a temperature of from about 20° to 130° C for from about 1 to 20 hours. The azide used in the reaction is preferably ammonium or an alkali metal azide, e.g. sodium or lithium azide, but other azides, e.g. aluminium azide or the azides of nitrogen containing bases, e.g. mono-, di-, tri-, and tetra- methyl- ammonium, anilinium, morpholinium and piperidinium azides, may also be used if desired. Where an azide other than that of an alkali metal is used this azide may be prepared in the reaction mixture by double decomposition. The reaction may, if desired, be carried out in the presences of an electron acceptor, e.g. aluminium chloride, boron trifluoride, ethyl sulphonic acid or benzene sulphonic acid. As an alternative to the reaction conditions set out above, the reaction may be carried out using hydrazoic acid (hydrogen azide) at a temperature of from about 20° to 150° C in a suitable solvent, under greater than atmospheric pressure. When an azide other than hydrazoic acid is used, e.g. sodium azide, the product of the reaction will be the corresponding tetrazole salt. This salt may readily be converted to the free acid by treatment with strong acid, e.g. hydrochloric acid. Process (a) is believed to pass through a compound of formula XVIII as an intermediate. The good leaving group Z may be an alkoxy, thiol or alkylthio group, e.g. a lower alkoxy or a lower alkyl thiol group.

In process (b) the group X may be, for example, an aralkyl, e.g. a benzyl group; an arylacyl, e.g. a phenacyl group; an acyl, e.g. acetyl group; an amino group; or a group —(CH₂)₂G, where G is an electron withdrawing group, for example a nitrile, a carboxylic ester, e.g. of a lower alkanol, or an acyl group, e.g. an acetyl group.

When X represents an aralkyl group the group may be removed either using a hydrogen halide, e.g. HBr, in acetic acid or by catalytic hydrogenation using, for example, a palladium catalyst in a solvent which is inert under the reaction conditions, e.g. ethanol.

When X represents an acyl group, the group may be removed under mildly basic conditions with, for example, aniline or sodium bicarbonate.

When X represents a group —CH₂CH₂G the group may be removed under mildly basic conditions with, for example, barium hydroxide.

When X represents an amino group, the group may be removed by reductive de-amination with, for example, hypophosphorous acid, stannous chloride or sodium in liquid ammonia.

The cyclisation of process (c) may be carried out by heating, or under basic or neutral conditions. It is however preferred to carry out the cyclisation in the presence of an acid, e.g. hydrochloric acid, and in a solvent which is inert under the reaction conditions, e.g. ethanol. The reaction may be carried out at from about 20° to 150° C. It will be appreciated that the compound of formula VIII may also exist in a keto form, and this form is included in the definition of formula VIII. The compound of formula VIII may, if desired be used in the form of an alkali metal salt thereof.

In process (d) the dehydrogenation may be carried out by oxidation using a mild oxidizing agent, for example selenium dioxide, palladium black, chloranil, lead tetraacetate or triphenylmethyl perchorate. Alternatively the dehydrogenation may be carried out indirectly by halogenation followed by dehydrohalogenation, e.g. by treatment with N-bromosuccinimide or pyridinium bromide perbromide to yield the 3-bromo derivative which is subsequently dehydrobrominated. The reaction may be carried out in a solvent which is inert under the reaction conditions, e.g. a halogenated hydrocarbon, xylene or glacial acetic acid. The reaction may be carried out at an elevated temperature, e.g. from about 20° to 150° C.

In process (e) the hydrogenation may be carried out using catalystic hydrogenation, for example using a palladium on charcoal catalyst in a suitable solvent, e.g. ethanol. The reaction may conveniently be carried out at from about 20° to 80° C, preferably at slightly greater than atmospheric pressure.

In process (f) the replacement of the group —R⁹ by hydrogen may be carried out when R⁹ is an alkyl, e.g. a lower alkyl such as ethyl, or aralkyl, e.g. benzyl, group using an acid, e.g. HCl in ethanol, aqueous HBr, or HBr in glacial acetic acid. Where R⁹ is an acyl, e.g. a lower alkanoyl such as acetyl, group the reaction may be carried out under mild alkaline conditions and where R⁹ is an aralkyl, e.g. a benzyl group, the reaction may be carried out hydrogenation. These reactions may be carried out at an elevated temperature.

The transformation of process (g) may be effected by warming in a solvent which is inert under the reaction conditions, e.g. ethanol. The reaction may be carried out under acidic or neutral conditions, but is preferably carried out in the presence of a base, e.g. sodium hydroxide, in a solvent which is inert under the reaction conditions, e.g. water or ethanol. The reaction is also preferably carried out in dilute, e.g. about 1%, solution and may be carried out at from about 15° to 35° C.

The compounds of formula II in which Y is a group —CN may be made by dehydrating the corresponding compound of formula IV,

  IV in which R is as defined above, using, for example, phosphorus oxychloride, as dehydrating agent. The reaction is preferably carried out using at least one molar equivalent of dehydrating agent per mole of compound of formula IV. Where the dehydrating agent reacts with one of $R_5$, $R_6$, $R_7$ or $R_8$ (e.g. a substituent comprising an —OH group) sufficient dehydrating agent should be used to satisfy the side reaction as well as the main reaction. The reaction may, if desired, be carried out in the presence of an acid binding agent, e.g. triethylamine. The reaction may be carried out in the presence of a solvent, e.g. N,N-dimethylformamide, dimethyl sulphoxide, pyridine, benzene or hexamethyl phosphoramide, or an excess of the dehydrating agent may be used as the reaction medium. The reaction may be carried out at a temperature of from about 0° to 200° C depending on the dehydrating agent used. When phosphorus oxychloride is used a temperature of from 0° to 100° C is preferred.

The compounds of formula IV may be made by reacting a compound formula V,

  V in which R is as defined above, and $R^x$ is a lower alkyl group, with ammonia, using techniques conventional in the production of amides from esters, e.g. using an alkanol as solvent at a temperature of 0° to 120° C.

Compounds of formula II in which Y represents a group —CZ=NH may be made in a manner known per se from compounds of formula II in which Y is a group —CN, e.g. by reaction with an alkanol, a thiol or $H_2S$ in the presence of HCl.

The compounds of formulae VII may be made by reacting a compound of formula X,

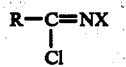  X in which R and X are as defined above, with an azide. The reaction may be carried out under substantially the same conditions as set out above for process (a).

The compounds of formula X may be made by reacting a compound of formula XI,

  XI in which R and X are as defined above, with phosphorus pentachloride.

The compounds of formula VII and XIV may also be made from compounds of formula I using techniques known per se, for example by reaction with a compound X Hal, in which X is as defined above and Hal represents a halogen atom. Compounds of formulae VII and XIV in which X is an amino group may be made by reacting a compound of formula I with hydroxylamine-O-sulphonic acid in weakly alkaline aqueous solution, and compounds of formula VII and XIV in which X represents a group —$CH_2CH_2G$ may also be made by Michael addition of a compound $CH_2$=CHG to a compound of formula I.

The compounds of formula VIII may be made by reaction of a compound of formula XII,

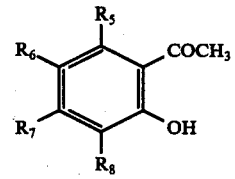  XII in which $R_5$, $R_6$, $R_7$, $R_8$ and the proviso are as defined above, with a compound of formula XIII,

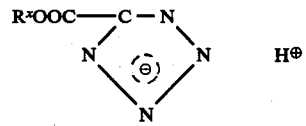  XIII in which $R^x$ is a lower alkyl group. The reaction may be carried out under conditions conventional for a Claisen condensation. Compounds of formula VIII may also be made by the action of mild alkali on a compound of formula I.

Compounds of formula XV may be made by selective hydrogenation of a corresponding compound of formula I, or by methods analogous to process (a) above using the corresponding chromanone-2-carboxylic acid (via the nitrile) as starting material.

Compounds of formula XVI and XVII are either compounds of formula I or may be made in a manner analogous to the methods given above for making the compounds of formula I.

The compounds of formula V, XI, XII, and XIII are either known or may be made from known starting material using conventional techniques.

It will be appreciated that while the unsubstituted tetrazole group has been represented above in a delocalised form other representations of the same group are also commonly used.

Some of the substituents $R_5$, $R_6$, $R_7$ and $R_8$ may be affected by the reaction conditions (either in the final steps or in the production of intermediates) described above. It is therefore contemplated that where necessary or desirable the reactions be carried out using simple derivatives of the reagents. Thus in process (a) where one of $R_5$, $R_6$, $R_7$ or $R_8$ represents a hydroxyalkoxy group the compound of formula II may be used as an ester derivative or dihydropyranyl derivative of the hydroxy group and the resulting ester or dihydropyranyl derivative converted to a compound of formula I, e.g. by hydrolysis.

The compounds of formula I and the intermediates therefor may be recovered from their reaction mixtures using conventional methods.

The processes described above may produce the compound of formula I or a derivative thereof. It is also within the scope of this invention to treat any derivative so produced to liberate the free compound of formula I, or to convert one derivative into another.

Pharmaceutically acceptable derivatives of the compounds of formula I include pharmaceutically acceptable salts. Suitable salts include water soluble salts, for example ammonium, alkali metal (e.g. sodium, potassium and lithium) and alkaline earth metal (e.g. calcium or magnesium,) salts and salts with suitable organic bases, e.g. salts with lower alkyl amines, e.g. methylamine or ethylamine, with substituted lower alkylamines, e.g. hydroxy substituted alkylamines, or with simple monocyclic nitrogen heterocyclic compounds, e.g. piperidine or morpholine.

The compounds of formula I and pharmaceutically acceptable derivatives thereof are useful because they possess pharmacological activity in animals; in particular they are useful because they inhibit the release and-/or action of pharmacological mediators which result from the in vivo combination of certain types of antibody and specific antigen e.g. the combination of reaginic antibody with specific antigen (see Example A). In man, both subjective and objective changes which result from the inhalation of specific antigen by sensitised subjects are inhibited by prior administration of the compounds. Thus the compounds are useful in the treatment of asthma, e.g. allergic asthma. The compounds are also useful in the treatment of so-called 'intrinsic' asthma (in which no sensitivity to extrinsic antigen can be demonstrated). The compounds are also of use in the treatment of other conditions in which antigen-antibody reactions are responsible for disease, for example, hay fever and urticaria.

For the above mentioned uses the dosage administered will, of course, vary with the compound employed, the mode of administration and the treatment desired. However, in general, satisfactory results are obtained when the compounds are administered at a dosage of from 0.1 to 50 mg per kg of animal body weight in the test set out in Example A. For man the total daily dosage is in the range of from about 1 mg to 3,500 mg which may be administered in divided doses from 1 to 6 times a day or in sustained released form. Thus dosage forms suitable for administration (by inhalation or oesophageally) comprise from about 0.17 mg to 600 mg, preferably 30 to 600 mg, of the compound admixed with a solid or liquid pharmaceutically acceptable diluent, adjuvant or carrier.

According to the invention there is also provided a process for the production of a pharmaceutically acceptable salt of a compound of formula I, which comprises treating a compound of formula I, or another salt thereof, with a compound, e.g. a base or ion exchange resin, containing an availabe pharmaceutically acceptable cation, e.g. sodium, potassium, calcium, ammonium, and appropriate nitrogen containing cations. In general we prefer to form the pharmaceutically acceptable salt by treating the free acid of formula I with an appropriate base, e.g. with an alkaline-earth or alkali metal hydroxide, carbonate or bicarbonate in aqueous solution or by treating a salt of a compound of formula I with another salt by a metathetical process. When a strongly basic compound is used care should be taken, e.g. by keeping the temperature sufficiently low, to ensure that the compound of formula I is not hydrolysed or otherwise degraded. The pharmaceutically acceptable salt may be recovered from the reaction mixture by, for example, solvent precipitation and/or removal of the solvent by evaporation, e.g. by freeze drying.

Values of $R_5$, $R_6$, $R_7$ and $R_8$ which may be mentioned include hydrogen, straight or branched alkyl, e.g. containing from 2 to 5 carbon atoms, straight or branched alkoxy, e.g. containing from 2 to 6 carbon atoms, or hydroxy-alkoxy containing from 3 to 5 carbon atoms.

In this specification and in the claims the term 'lower', e.g. as applied to alkyl or alkoxy groups, means that the group contains up to 6 carbon atoms.

An especially preferred group of the compounds of formula I are those in which, $R_5$ is hydrogen, alkoxy containing from 2 to 6 carbon atoms, (preferably branched chain alkoxy), hydroxy, or hydroxy-alkoxycontaining 3 to 6 carbon atoms, $R_6$ is hydrogen or branched chain alkyl, $R_7$ is hydrogen, and $R_8$ is hydrogen or alkyl containing 2 to 6 carbon atoms, provided that one or two $R_5$, $R_6$, $R_7$ and $R_8$ is other than hydrogen.

The compounds of formula I, and pharmaceutically acceptable derivatives thereof (and in particular the salts, e.g. the alkali metal salts, thereof) have the advantage that they are more readily absorbed and are more active when administered oesophageally than compounds of similar structure.

According to our invention we also provide a pharmaceutical composition comprising (preferably a minor proportion of) a compound of formula I, or a pharmaceutically acceptable derivative thereof, in combination with a pharmaceutically acceptable adjuvant, diluent or carrier. Examples of suitable adjuvants, diluents or carriers are:- for tablets and dragees; lactose, starch, talc or stearic acid; for capsules, tartaric acid or lactose; for suppositories, natural or hardened oils or waxes; for inhalation compositions, coarse lactose. For use in inhalation compositions the compounds of formula I, or the pharmaceutically acceptable derivative thereof, preferably has a fine particle size of from 0.01 to 10 microns and may if desired be used in combination with a bronchodilator, e.g. isoprenaline. The compound of fine particle size may be made, for example by grinding or milling. The compositions may also contain suitable preserving, stabilising and wetting agents, solubilizers, sweetening and colouring agents and flavourings. The compositions may, if desired, be formulated in sustained release form. We prefer compositions which are designed to be taken oesophageally and to release their contents in the gasto-intestinal tract.

Compositions for inhalation may also comprise a solution, e.g. an aqueous solution, of the compound of formula I or the pharmaceutically acceptable derivative thereof; or may comprise a mixture of the compound with a liquifyable gas under pressure, the mixture being put up in a container having a valve adapted to dispense a metered dose.

The invention is illustrated, but in no way limited by the following Examples, in which the parts are by weight. Example 1 does not relate to a compound according to the invention.

EXAMPLE 1

5-(6-Chloro-5,7-dimethyl-4-oxo-4H-1-benzopyran-2-yl)tetrazole a. 6-Chloro-5,7-dimethyl-4-oxo-4H-1-benzopyran-2-carboxylic acid 0.5 Parts of benzyl trimethylammonium hydroxide were added dropwise to a mixture of 156.6 parts of 4-chloro-3, 5-xylenol, 149.1 parts of dimethyl acetylene dicarboxylate and 30 parts of dioxan. The reaction mixture was heated for ½ hour on the steam bath, cooled, and basified with 320 parts of 25% aqueous sodium hydroxide solution. After addition of 100 parts of methanol the red solution was heated at reflux for 3 hours on the steam bath, cooled, and acidified with excess dilute sulphuric acid. The precipitated yellow solid was filtered, washed with a little water, and dried. The solid was added portionwise to 850 parts of stirred chlorosulphonic acid cooled to 0° C. When all the solid had dissolved, the dark red solution was added cautiously dropwise to excess ice-water. The precipitated solid was filtered, washed with water, and recrystallised from a dioxan aqueous ethanol mixture to give 157.1 parts of 6-chloro-5,7-dimethyl-4-oxo-4H-1-benzopyran-2-carboxylic acid as a colourless solid, melting point 289°–290° C.

Analysis:
Found: C,56.9; H,3.53; Cl,14.1% $C_{12}H_9ClO_4$ requires: C,57.1; H,3.59; Cl,14.03%

Spectral confirmation

Molecular weight = 252/254 by mass spectrometry. IR acid carbonyl absorption occurred at 1740 $cm^{-1}$ and benzopyran carbonyl absorption at 1634 $cm^{-1}$. The NMR spectrum included a singlet at 3.3$\tau$ due to the benzopyran ring 3-proton.

b. 6-Chloro-5,7-dimethyl-4-oxo-4H-1-benzopyran-2-carboxylic acid, ethyl ester

10 Parts of concentrated sulphuric acid were added to a suspension of 66.1 parts of 6-chloro-5,7-dimethyl-4-oxo-4H-1-benzopyran-2-carboxylic acid in 600 parts of ethanol, and the mixture was heated at reflux for 24 hr. Most of the ethanol was removed by evaporation under reduced pressure, and 1500 parts of water were added to the reaction mixture. The precipitated solid was filtered, dissolved in chloroform and the solution, dried and evaporated, leaving 58.5 parts of 6-chloro-5,7-dimethyl-4-oxo-4H-1-benzopyran-2-carboxylic acid, ethyl ester as a colourless solid. On recrystallisation from ethanol, the product had melting point 114.5°–115.5° C.

Analysis:
Found: C,60.2; H,4.73; Cl,12.89% $C_{14}H_{13}ClO_4$ requires: C,59.9; H,4.67; Cl,12.63%

Spectral confirmation

Molecular weight = 280/282 by mass spectrometry. IR ester carbonyl absorption was evident at 1740 $cm^{-1}$ and the presence of the ester group was confirmed by NMR absorptions at 8.6 (triplet) and 5.5 (quartet). (Solvent: deuterochloroform).

c. 6-Chloro-5,7-dimethyl-4-oxo-4H-1-benzopyran-2-carboxamide

A solution of 50.1 parts of 6-chloro-5,7-dimethyl-4-oxo-4H-1-benzopyran-2-carboxylic acid ethyl ester in 750 parts of warm ethanol was saturated with dry ammonia. After 2 hours a solid had precipitated out and the slurry was heated on the steam bath to remove excess ammonia. The solid was filtered off and crystallised from dimethylformamide to give 42.3 parts of 6-chloro-5,7-dimethyl-4-oxo-4H-1-benzopyran-2-carboxamide, melting point >300° C.

Analysis:
Found: C,57.0; H,3.83; Cl,14,02; N,5.45% $C_{12}H_{10}O_3Cl$ requires: C,57.3; H,4.00; Cl,14.09; N,5.57% d. 6-Chloro-5,7-dimethyl-4-oxo-4H-1-benzopyran-2-carbonitrile

To 400 parts of N,N-dimethylformamide was slowly added 21 parts of phosphorus oxychloride with stirring and ice cooling. Then in small quantities 33.9 parts of 6-chloro-5,7-dimethyl-4-oxo-4H-1-benzopyran-2-carboxamide was added to the solution. After the addition was completed the reaction mixture was stirred at room temperature for 18 hours. The dark solution which resulted was poured into 1500 parts of ice/water. The precipitated solid was filtered off and crystallised from ethanol to give 30.5 parts of 6-chloro-5,7-dimethyl-4-oxo-4H-1-benzopyran-2-carbonitrile, melting point 142°–143° C.

e. 5-(6-Chloro-5,7-dimethyl-4-oxo-4H-1-benzopyran-2-yl) tetrazole

A mixture of 23.4 parts of 6-chloro-5,7-dimethyl-4-oxo-4H-1-benzopyran-2-carbonitrile, 7.8 parts of sodium azide, 6.4 parts of ammonium chloride and 200 parts of N,N-dimethylformamide was stirred and heated on the steam bath for 18 hours. Most of the solvent was then removed by distillation under reduced pressure. A solution of the residue in 400 parts of water was acidified with 20% hydrochloric acid. The precipitated solid was filtered off, washed with water and crystallised from dioxan to give 15.5 parts of 5-(6-chloro-5,7-dimethyl-4-oxo-4H-1-benzopyran-2-yl) tetrazole as a colourless solid, melting point 246°–247° C (decomposition).

Analysis:
Found: C,52.3; H,3.39; N,19.78; Cl,12.6% $C_{12}H_9ClN_4O_2$ requires: C,52.1; H,3.28; N,20.24; Cl,12.81%

Spectral confirmation

The mass spectral molecular weight was 276/278. An IR peak at 1660 $cm^{-1}$ was assigned to the benzopyran ring carbonyl.

f. 5-(6-Chloro-5,7-dimethyl-4-oxo-4H-1-benzopyran-2-yl)tetrazole, sodium salt

A mixture of 5.01 parts of 5-(6-chloro-5,7-dimethyl-4-oxo-4H-1-benzopyran-2-yl)tetrazole and 1.52 parts of sodium bicarbonate was dissolved in 50 parts of water. The filtered solution was freeze-dried to give 5.20 parts of 5-(6-chloro-5,7-dimethyl-4-oxo-4H-1-benzopyran-2-yl)tetrazole, sodium salt. The salt was purified by precipitation from an ethanolic solution by addition of ether.

Spectral confirmation

The benzopyran ring carbonyl gave rise to a broad IR band at 1645 $cm^{-1}$. The NMR spectrum showed a singlet at 4.2$\tau$ due to the benzpyran ring 3-proton. (solvent: deuterium oxide).

EXAMPLE 2

5-[5-(2-Hydroxypropoxy)-4-oxo-4H-1-benzopyran-2-yl]tetrazole a. 5-(2-Hydroxypropoxy)-4-oxo-4H-1-benzopyran-2-carboxamide By the Method of Example 1 (c) 32 parts of 5-(2-hydroxy propoxy)-4-oxo-4H-1-benzopyran-2-carboxylic acid, ethyl ester were treated with ethanolic ammonia to give 23.3 parts of 5-(2-hydroxy propoxy)-4-oxo-4H-1-benzopyran-2-carboxamide, which crystallised from a mixture of ethanol and chloroform as a white solid, melting point 229°–231° C.

b. 5-(2-Formyloxypropoxy)-4-oxo-4H-1-benzopyran-2-carbonitrile

By the method of Example 1 (d) 25.4 parts of the product of step (a) were treated with 30 parts of phosphorus oxychloride to give 14.9 parts of 5-(2-formyloxypropoxy)-4-oxo-4H-1-benzopyran-2-carbonitrile, which crystallised from ethanol as a pink solid, melting point 113°–115° C. The structure of this product was confirmed by infra-red and nuclear magnetic resonance spectroscropy.

c. 5-[5-(2-Hydroxypropoxy)-4-oxo-4H-1-benzopyran-2-yl] tetrazole

By the method of Example 1 (e) 11.7 parts of the product of step (b) were treated with 3.05 parts of sodium azide and 2.54 parts of ammonium chloride to give 12.4 parts of 5-[5-(2-hydroxy propoxy)-4-oxo-4H-1-benzopyran-2-yl]tetrazole as a white solid, melting point 299° C (decomposition).

d. 5[5-(2-Hydroxypropoxy)-4-oxo-4H-1-benzopyran-2-yl] tetrazole, sodium salt.

A mixture of 10.6 parts of the product of step (c) and 3.10 parts of sodium bicarbonate was dissolved in water. The solvent was removed from the solution by distillation under reduced pressure. The yellow residue was crystallised four times from ethanol to give 3.0 parts of 5-[5-(2-hydroxypropoxy)-4-oxo-4H-1-benzopyran-2-yl]-tetrazole, sodium salt as a white solid, melting point 290° C (decomposition).

Analysis:
Found: C,50.5; H,3.50; N,17.74; Na,7.10%
$C_{13}H_{11}N_4NaO_4$ requires: C,50.3; H,3.55; N,18.06; Na,7.41%

EXAMPLE 3

5-[5-(3-methyl-n-butoxy)-4-oxo-4H-1-benzopyran-2-yl]tetrazole a. 5-[2,3-Dihydro-5-(3-methyl-n-butoxy)-4-oxo-4H-1-benzopyran-2-yl]tetrazole To a solution of 1 part of 5-[5-(3-methyl-n-butoxy)-4-oxo-4H-1-benzopyran-2-yl]tetrazole in 50 parts of ethanol was added 5 parts of Raney nickel catalyst. The resulting mixture was hydrogenated at 20° C and 45 lbs/sq. in. pressure for 8 hours. The catalyst was filtered off and the filtrate was evaporated to give an oil which solidified on trituration with petroleum ether (b.p. 40°–60° C). This solid was crystallised from a mixture of ethyl acetate and petroluem ether (b.p. 40°–60° C) to give 0.2 parts of 5-[2,3-dihydro-5-(3-methylbutoxy)-4-oxo-4H-1-benzopyran-2-yl] tetrazole as a white solid, m.p. 134°–137° C. The structure of this product was confirmed by n.m.r. and m.s. measurements.

b. 5-[5-(3-methyl-n-butoxy)-4-oxo-4H-1-benzopyran-2-yl] tetrazole

A solution of 0.3 parts of 5-[2,3-dihydro-5-(3-methyl-n-butoxy)-4-oxo-4H-1-benzopyran-2-yl]tetrazole and 0.44 parts of selenium dioxide in 20 parts of amyl alcohol was heated under gentle reflux for 8 hours. After cooling, ether was added to the reaction mixture, the resulting precipitate was filtered off and the filtrate was evaporated to give a solid which was crystallised from a mixture of ethyl acetate and petroleum ether (b.p. 40°–60° C) giving 5-[5-(3-methyl-n-butoxy)-4-oxo-4H-1-benzopyran-2-yl]tetrazole as colourless prisms, m.p. 165°–166° C.

EXAMPLE 4

The amides listed in Table II were prepared, from the appropriate ethyl esters, using the method of Example 1(c).

TABLE II

| Name of Compound | M.P. ° C | Elemental Analysis Found | | |
|---|---|---|---|---|
| | | C | H | N |
| 6,8-Di-t-butyl-4-oxo-4H-1-benzopyran-2-carboxamide | 255–257 | 71.88 | 7.88 | 4.6 |
| 5-(3-Methyl-n-butoxy)-4-oxo-4H-1-benzopyran-2-carboxamide | 170–171 | 64.6 | 6.24 | 4.9 |
| 5-Hydroxy-4-oxo-4H-1-benzopyran-2-carboxamide | 319–321 | 58.7 | 3.45 | 6.87 |

EXAMPLE 5

The nitriles listed in Table III were prepared from the corresponding amides, using the method of Example 1(d).

TABLE III

| Name of Compound | M.P. ° C | Elemental Analysis Found | | |
|---|---|---|---|---|
| | | C | H | N |
| 6,8-Di-t-butyl-4-oxo-4H-1-benzopyran-2-carbonitrile | 106–107 | 76.7 | 7.72 | 4.92 |
| 5-(3-Methyl-n-butoxy)-4-oxo-4H-1-benzopyran-2-carbonitrile | 83.5–84.5 | 69.75 | 5.88 | 5.36 |
| 5-Hydroxy-4-oxo-4H-1-benzopyran-2-carbonitrile | 130–131 | 63.8 | 2.67 | 7.52 |

EXAMPLE 6

The tetrazoles listed in Table IV were prepared from the corresponding nitriles, using the method of Example 1(e). The sodium salts of the tetrazoles listed in Table IV were prepared by the process of Example 1(f).

TABLE IV

| Name of Compound | M.P. ° C | Elemental Analysis Found | | |
|---|---|---|---|---|
| | | C | H | N |
| 5-(6,8-Di-t-butyl-4-oxo-4H-1-benzopyran-2-yl) tetrazole | 236–238.5 | 66.5 | 6.92 | 16.96 |
| 5-[3-(3-methyl-n-butoxy)-4-oxo-4H-1-benzopyran-2-yl]tetrazole | 165–168 | 60.0 | 5.39 | 18.36 |
| 5-(5-Hydroxy-4-oxo-4H-1-benzopyran-2-yl) tetrazole | 271–272 | 52.1 | 2.43 | 23.95 |

EXAMPLE 7

5-[5-(3-methyl-n-butoxy)-8-n-propyl-4-oxo-4H-1-benzopyran-2-yl]tetrazole

A solution of 1.0 parts of 5-[8-allyl-5-(3-methyl-n-butoxy)-4H-1-benzopyran-2-yl]tetrazole in 19 parts of ethanol was hydrogenated overnight at room temperature and pressure using 0.02 parts of 5% palladium on charcoal as catalyst. The reaction mixture was filtered and the solvent removed by evaporation. Cystallisation of the residue from ethanol gave 0.52 parts of 5-[5-(3-methyl-n-butoxy)-8-n-propyl-4-oxo-4H-1-benzopyran-2-yl]tetrazole, m.p. 202°–204° C.

Spectral confirmation

Molecular weight (Mass Spectroscopy)
Found: 342 $C_{18}H_{22}N_4O_3$ requires: 342

EXAMPLE 8

5-[5-(3-methyl-n-butoxy)-8-n-propyl-4-oxo-4H-1-benzopyran-2-yl] tetrazole a. 5-[8-allyl-5-(3-methyl-n-butoxy)-4-oxo-4H-1-benzopyran-2-yl]-N-benzyl tetrazole A mixture of 30 parts of 5-[8-allyl-5-(3-methyl-n-butoxy)-4-oxo-4H-1-benzopyran-2-yl]tetrazole, 16.6 parts of benzyl bromide, 3.53 parts of sodium hydroxide, 120 parts of ethanol and 60 parts of water was refluxed for 64 hours. The mixture was cooled, was extracted with chloroform and the chloroform extract washed with sodium bicarbonate solution and water. Evaporation of the chloroform gave a residue which was chromatographed on silica gel. Elution with 3 : 1 toluene/acetic acid and chloroform gave, after crystallisation from ethanol, a total of 7.31 parts of 5-[8-allyl-5-(3-methyl-n-butoxy)-4-oxo-4H-1-benzopyran-2-yl]-N-benzyltetrazole, m.p. 92.5–94° C.

Spectral Confirmation

Molecular weight (Mass Spectroscopy)
Found: 430 $C_{25}H_{26}O_3N_4$ requires 430
The n.m.r. spectrum in hexadeuterodimethyl sulphoxide confirmed the structure.

b. 5-[5-(3-methyl-n-butoxy)-8-n-propyl-4-oxo-4H-1-benzopyran-2-yl]-N-benzyltetrazole 1. A solution of 5.34 parts of 5-[8-allyl-5-(3-methyl-n-butoxy)-4-oxo-4H-1-benzopyran-2-yl]-N-benzyltetrazole in 1000 parts of ethanol was hydrogenated at room temperature and pressure for 20 hours using 0.14 parts of 5% palladium on charcoal as catalyst. The reaction mixture was filtered and the solvent removed by evaporation. Crystallisation of the residue from chloroform/light petroleum (40:60) gave 1.89 parts of 5-[5-(3-methyl-n-butoxy)-8-n-propyl-4-oxo-4H-1-benzopyran-2-yl]-N-benzyltetrazole, m.p. 87°–87.5° C.

Spectral Confirmation

Molecular weight (Mass Spectroscopy)
Found: 432 $C_{25}H_{28}O_3N_4$ requires 432
The n.m.r. spectrum in hexadeuterodimethyl sulphoxide confirmed the structure.

2. A mixture of 10 parts of 5-[5-(3-methyl-n-butoxy)-8-n-propyl-4-oxo-4H-1-benzopyran-2-yl]tetrazole, 5.5 parts of benzyl bromide, 1.14 parts of sodium hydroxide, 40 parts of ethanol and 20 parts of water was refluxed for 2 1/2 days. The volatile components of the mixture were then removed by evaporation under reduced pressure to give a residue which was chromatographed on silica gel. Elution with ethyl acetate and chloroform gave, after crystallisation from ethanol, a total of 2.98 parts of 5-[5-(3-methyl-n-butoxy)-8-n-propyl-4-oxo-1-benzopyran-2-yl]-N-benzyltetrazole, m.p. 88°–88.5° C.

Spectral Confirmation

Molecular weight (Mass Spectroscopy)
Found: 432 $C_{25}H_{28}O_3N_4$ requires 432
The n.m.r. spectrum in hexadeuterodimethyl sulphoxide confirmed the structure.

c. 5-[5-(3-methyl-n-butoxy)-8-n-propyl-4-oxo-4H-1-benzopyran-2-yl] tetrazole

A solution of 2.96 parts of 5-[5-(3-methyl-n-butoxy)-8-n-propyl-4-oxo-4H-1-benzopyran-2-yl]-N-benzyltetrazole in 500 parts of ethanol was stirred at 60° C, with 0.096 parts of 5% palladium on charcoal, in an atmosphere of hydrogen for 11 1/2 hours. The reaction mixture was cooled, was filtered and the solvent removed by evaporation to give a residue which was chromatographed on silica gel. Careful elution with chloroform and chloroform/acetone gave 0.16 parts of 5-[5-(3-methyl-n-butoxy)-8-n-propyl-4-oxo-4H-1-benzopyran-2-yl]tetrazole, m.p. 199°–200° C (after recrystallisation from ethanol).

Spectral Confirmation

Molecular weight (Mass Spectroscopy)
Found : 342 $C_{18}H_{22}O_3N_4$ requires: 342

EXAMPLE 9

5-[5-hydroxy-8-n-propyl-4-oxo-4H-1-benzopyran-2-yl]tetrazole

A mixture of 5 parts of 5-[5-(3-methyl-n-butoxy)-8-n-propyl-4-oxo-4H-1 -benzopyran-2-yl]tetrazole in 130 parts by volume of 48% aqueous hydrobromic acid was refluxed for 3 hours, then cooled and water added. The resulting mixture was neutralised by the addition of solid sodium bicarbonate, then made slightly acidic by re-acidification with dilute hydrochloric acid and extracted with chloroform. The chloroform extract was washed with saturated brine and water, and was dried. Evaporation of the chloroform gave a solid which was purified by precipitation from aqueous ethanol to give 0.36 parts of 5-[5-hydroxy-8-n-propyl-4-oxo-4H-1-benzopyran-2-yl]tetrazole, m.p. 242.5°–245° C.

Spectral Confirmation

Molecular weight (Mass Spectroscopy)
Found : 272 $C_{13}H_{12}O_3N_4$ requires : 272

EXAMPLE A

The procedure set out below may be used to assess the effectiveness of a compound in inhibiting the release of the pharmacological mediators of anaphylaxis.

In this test, the effectiveness of the compounds in inhibiting the passive cutaneous anaphylactic reaction in rats is assessed. It has been proved that this form of test gives reliable qualitative indications of the ability of the compounds under test to inhibit antibody-antigen reactions in man.

In this test method Charles River France/Fisons bred rats (male or female) having a body of from 100 to 150 gms are infected subcutaneously at weekly intervals with N.brasiliensis larvae in doses increasing from about 2000 larvae per animal to 12,000 larvae per animal in order to establish the infection. After 8 weeks the rats are bled by heart puncture and 15–20 mls. of blood are collected from each animal. The blood samples are then centrifuged at 3500 rpm. for 30 minutes in order to remove the blood cells from the blood plasma. The serum is collected and used to provide a serum containing N.brasiliensis antibody. A pilot sensitivity test is carried out to determine the least quantity of serum required to give a skin weal in control animals in the test described below of 2 cm diameter. It has been found that optimum sensitivity of rats in the body weight range 100–130 gms is obtained using a serum diluted with eight parts of physiological saline solution. This diluted solution is called antibody serum A.

The antigen to react with the antibody in serum A is prepared by removing N. brasiliensis worms for the gut of the infected rats, centrifuging the homogenate and collecting the supernatent liquor. This liquor is diluted with saline to give a protein content of 1 mg/ml and is known as solution B.

Charles River France/Fisons bred rats in the body weight range 100 to 130 gms are sensitised by intra-dermal injection of 0.1 mils of serum A into the right flank. Sensitivity is allowed to develop for 24 hours and the rats are then injected intravenously with 1 ml/100 gms body weight of a mixture of solution B (0.25 mls), Evans Blue dye solution (0.25 mls) and the solution of the compound under test (0.5 mls with varying percentages of active matter). Insoluble compounds are administered as a separate intraperitoneal injection 5 minutes before intravenous administration of solution B and Evans Blue dye. For each percentage level of active matter in the solution under test five rats are injected. Five rats are used as controls in each test. The dosages of the compound under test are selected so as to give a range of inhibition values.

Thirty minutes after injection of solution B the rats are killed and the skins are removed and reversed. The intensity of the anaphylactic reaction is assessed by comparing the size of the characteristic blue weal produced by the spread of the Evans Blue dye from the sensitisation site, with the size of the weal in the control animals. The size of the weal is rated as 0 (no weal detected, i.e. 100% inhibition) to 4 (no difference in size of weal, i.e. no inhibition) and the percentage inhibition for each dose level calculated as:

$$\% \text{ inhibition} = \frac{(\text{Control group score} - \text{treated group score}) \times 100}{\text{Control group score}}$$

The percentage inhibitions for the various dose levels are plotted graphically for each compound. From these graphs the dosage required to achieve a 50% inhibition of the anaphylactic reaction ($ID_{50}$) may be determined.

The compounds are also evaluated in the above manner using intestinal and gastric administration of the compound.

EXAMPLE B

| Tablet | |
|---|---|
| Compound of formula I, e.g. 5-[5-(3-methyl-n-butoxy)-4-oxo-4H-1-benzopyran-2-yl] tetrazole, sodium salt | 50 mg |
| Binder, e.g. powdered tragacenth | 1 to 3% |
| Lubricant, e.g. magnesium stearate | 0.25 to 1% |
| Disintegrating agent e.g. potato starch | 5 to 10% |
| Surfactant, e.g. di-octylsodium sulphosuccinate | 0.25% |

EXAMPLE C

| Capsule (Hard) | |
|---|---|
| Sodium salt of compound of formula I | 500 mg |
| Granulating agent, e.g. gum or starch mucilage | q.s. |
| Lubricant, e.g. magnesium stearate | 0.25 to 1% |

EXAMPLE D

| Capsule (Soft) | |
|---|---|
| Sodium salt of compound of formula I | 500 mg |
| Polyethylene glycol 400 | q.s. |
| Non-ionic surfactant, e.g. poloxy ethylene sorbitan mono-oleate | q.s. |

EXAMPLE E

| Suppository | |
|---|---|
| Sodium salt of compound of formula I | 500 mg |
| Basis, e.g. polyethylene glycol 6,000 | 1 g |

We claim:

1. A pharmaceutical composition comprising: 5-(5-hydroxy-4-oxo-4H-1-benzopyran-2-yl)tetrazole or a pharmaceutically acceptable salt thereof as active ingredient, in combination with a pharmaceutically acceptable adjuvant, diluent or carrier.

2. A method for treatment of allergic asthma which comprises administering 1 to 3500 mg. per day of 5-(5-hydroxy-4-oxo-4H-1-benzopyran-2-yl)tetrazole, to an asthmatic patient.

3. A pharmaceutical composition comprising: 5[6,8-di-t-butyl-4-oxo-4H-1-benzopyran-2-yl]tetrazole or a pharmaceutically acceptable salt thereof as active ingredient, in combination with a pharmaceutically acceptable adjuvant, diluent or carrier.

4. A method for treatment of allergic asthma which comprises adminstering 1 to 3500 mg. per day of 5[6,8-di-t-butyl-4-oxo-4H-1-benzopyran-2-yl]tetrazole, to as asthmatic patient.

* * * * *